US010159673B2

(12) United States Patent
Erickson et al.

(10) Patent No.: US 10,159,673 B2
(45) Date of Patent: *Dec. 25, 2018

(54) COMPOSITIONS AND METHODS FOR TREATMENT OF FRAGILE X SYNDROME

(71) Applicant: Children's Hospital Medical Center, Cincinnati, OH (US)

(72) Inventors: Craig Erickson, Cincinnati, OH (US); Tori Lynn Schaefer, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/818,850

(22) Filed: Nov. 21, 2017

(65) Prior Publication Data

US 2018/0104244 A1  Apr. 19, 2018

Related U.S. Application Data

(63) Continuation of application No. 14/994,705, filed on Jan. 13, 2016, now Pat. No. 9,844,551.

(60) Provisional application No. 62/103,126, filed on Jan. 14, 2015.

(51) Int. Cl.
*A61K 31/5025* (2006.01)
*A61K 31/502* (2006.01)

(52) U.S. Cl.
CPC ........ *A61K 31/5025* (2013.01); *A61K 31/502* (2013.01)

(58) Field of Classification Search
None
See application file for complete search history.

(56) References Cited

U.S. PATENT DOCUMENTS

| | | | |
|---|---|---|---|
| 6,399,608 B1 | 6/2002 | Dawson | |
| 7,425,556 B2* | 9/2008 | Chapdelaine | C07D 237/28 514/248 |
| 9,844,551 B2 | 12/2017 | Erickson et al. | |

FOREIGN PATENT DOCUMENTS

WO  WO 1999/037303 A1  7/1999

OTHER PUBLICATIONS

CAPLUS 2009 122477.*
Tsiouris, J. et al, CNS Drugs 2004 vol. 18, pp. 687-703.*
Heulens et al., Behav Brain Res. 2012 vol. 229 pp. 244-249.*
Hall, S. et al., Psychoneuroendocrinology 2012 vol. 37, pp. 509-518.*
Alhambra, C., et al., "Development and SAR of functionally selective allosteric modulators of $GABA_A$ receptors," Bioorganic & Medicinal Chemistry, 2011, 19:2927-38, 12 pgs.
Angkustsiri, K., et al., "Fragile X Syndrome with Anxiety Disorder and Exceptional Verbal Intelligence," Am J Med Genet Part A, 2008, 146:376-9, 4 pgs.
Bailey, Jr., D.B., et al., "Medication Utilization for Targeted Symptoms in Children and Adults with Fragile X Syndrome: US Survey," Journal of Developmental and Behavioral Pediatrics, 2012, 33:62-9, 8 pgs.
Berry-Kravis, E., et al., Psychopharmacology in Fragile X Syndrome—Present and Future, Ment Retard Dev Disabil Res Rev, 2004, 10:42-8, 7 pgs.
Berry-Kravis, E.M., et al., "Effects of STX209 (Arbaclofen) on Neurobehavioral Function in Children and Adults with Fragile X Syndrome: A Randomized, Controlled, Phase 2 Trial," Sci Transl Med, 2012, vol. 4, issue 152, 8 pgs.
Bhattacharya, A., et al., "Genetic Removal of p70 S6 Kinase 1 Corrects Molecular, Synaptic, and Behavioral Phenotypes in Fragile X Syndrome Mice," Neuron 2012, 76(2):325-37, 24 pgs.
Bourin, M., et al. "The mouse light/dark box test," European Journal of Pharmacology, 2003, 463:55-65, 11 pgs.
Brunskill, E.W., et al., "Abnormal neurodevelopment, neurosignaling and behaviour in Npas3-deficient mice," Eur J Neurosci, 2005, 22:1265-76, 12 pgs.
Chen, L., et al., "Fragile X Mice Develop Sensory Hyperreactivity to Auditory Stimuli," Neuroscience, 2001, 103(4):1043-50, 8 pgs.
Ciaccio, C., et al., "Fragile X syndrome: a review of clinical and molecular diagnoses," Ital. J. Pediatrics, 2017, 43(30():1-12, 12 pgs.
Crawley, J., et al., "Preliminary Report of a Simple Animal Behavior Model for the Anxiolytic Effects of Benzodiazepines," Pharmacol Biochem Behav, 1980, 13:167-70, 4 pgs.
Curran, C.P., et al., "In Utero and Lactational Exposure to PCBs in Mice: Adult Offspring Show Altered Learning and Memory Depending on Cypla2 and Ahr Genotypes," Environ Health Perspect, 2011, 119:1286-93, 8 pgs.
Dahlhaus, R., et al., "Altered neuroligin expression is involved in social deficits in a mouse model of the fragile X syndrome," Behavioural Brain Research, 2010, 208:96-105, 10 pgs.
De Saint Jan, D., et al., "Activation of human α1 and α2 homomeric glycine receptors by taurine and GABA," J. Physiol. 2001, 535. 3:741-755, 15 pgs.
D'Hooge, R., et al., "Mildly Impaired Water Maze Performance in Male Fmr1 Knockout Mice," Neuroscience, 1997, 76(2):367-76, 10 pgs.

(Continued)

*Primary Examiner* — Heidi Reese
(74) *Attorney, Agent, or Firm* — Frost Brown Todd LLC

(57) ABSTRACT

Disclosed are methods of alleviating or preventing one or more symptoms associated with fragile X syndrome in an individual in need thereof via administration of a therapeutically effective amount of a GABA(A) alpha 2 and/or 3 partial agonist. The one or more symptoms may include impaired functional communication, anxiety, inattention, hyperactivity, sensory reactivity, autonomic nervous system dysregulation, aberrant eye gaze, self-injury, aggression, seizures, EEG abnormalities, including but not limited to, abnormal spectral analysis, event related potentials which may include auditory and visual responses, abnormalities in cortical responses as evoked by transcranial magnetic stimulation including resting and active motor thresholds and abnormal responses in measures of cortical inhibition and excitation, aberrant impaired cognitive function, compromised daily living skills, or a combination thereof.

9 Claims, 3 Drawing Sheets

(56) References Cited

OTHER PUBLICATIONS

D'Hulst. C., et al., "Decreased expression of the $GABA_A$ receptor in fragile X syndrome," Brain Research, 2006, 1121:238-45, 8 pgs.
D'Hulst, C., et al., "Expression of the GABAergic system in animal models for fragile X syndrome and fragile X associated tremor/ataxia syndrome (FXTAS)," Brain Research, 2009, 1253:176-83, 8 pgs.
D'Hulst, C., et al., "The $GABA_A$ receptor: a novel target for treatment of fragile X?", Trends in Neurosciences, 2007, 30(8):425-31, 7 pgs.
Dunlop, B.W., et al., "Tiagabine for social anxiety disorder," Human Psychopharmacology, 2007, 22:241-4, 4 pgs.
Egashira, N., et al., "Effects of mood stabilizers on marble-burying behavior in mice: Involvement of GABAergic system," Psychopharmacology, 2013, 226:296-305, 12 pgs.
El Idrissi, A., et al., "Decreased $GABA_A$ receptor expression in the seizure-prone fragile X mouse," Neuroscience Letters, 2005, 377:141-6, 6 pgs.
El Idrissi, A., et al., "Neuroendocrine Alterations in the Fragile X Mouse," Chapter 11, *Results Probl Cell Differ*, 2012, 54:201-21, 21 pgs.
El Idrissi, A., et al, "Taurine Improves Congestive Functions in a Mouse Model of Fragile X Syndrome," Adv Ecp Med Biol, 2009, pp. 191-198, 1 pg. Abstract only.
Erickson, C.A., et al., "Managing maladaptive behaviors in fragile X patients," Curr Psychiatry, 2006, 5(10):80-92, 8 pgs.
Fragile X Syndrome, National Fragile X Foundation, downloaded Jul. 31, 2017 from https://fragilex.org/fragile-x/fragile-x-syndrome/, 2 pgs.
Frankland, P.W., et al., "Sensorimotor gating abnormalities in young males with fragile X syndrome and Fmr1-knockout mice," Molecular Psychiatry, 2004, 9:417-25, 9 pgs.
Garber, K.B., et al., "Fragile X syndrome," Eur J Hum Genet., Jun. 2008, 16(6):666-72, 14 pgs.
Gibb, R., et al., "A method for vibratome sectioning of Golgi-Cox stained whole rat brain," Journal of Neuroscience Methods, 1998, 79:1-4, 4 pgs.
Goebel-Goody, S.M., et al., "Genetic manipulation of STEP reverses behavioral abnormalities in a fragile X syndrome mouse model," Genes, Brain, and Behavior, 2012, 11:586-600, 15 pgs.
Goldson, E., et al., "The Fragile X Syndrome," Development Medicine and Child Neurology, 1992, 34:822-32, 7 pgs.
Hagerman, R.J., et al., "Fragile X Syndrome and Selective Mutism," Am J Med Genet, 1999, 83:313-7, 5 pgs.
Hagerman, R.J., et al., "Psychopathology in Fragile X Syndrome," The American Journal of Orthopsychiatry, 1989, 59(1):142-52, 11 pgs.
Hall, S., et al., "Effects of intranasal oxytocin on social anxiety in males with fragile X syndrome," Psychoneuroendocrinology, 2012, 37:509-518, 10 pgs.
Henderson, C., et al., "Reversal of Disease-Related Pathologies in the Fragile X Mouse Model by Selective Activation of $GABA_B$ Receptors with Arbaclofen," Science Translational Medicine, 2012, vol. 4, issue 152, 11 pgs.
Heulens, I., et al., "Involvement and Therapeutic Potential of the GABAergic System in the Fragile X Syndrome," TheScientificWorldJournal, 2010, 10:2198-206, 9 pgs.
Heulens, I., et al., "Pharmacological treatment of fragile X syndrome with GABAergic drugs in a knockout mouse model," Behav Brain Res., 2012, 229:244-249, 6 pgs.
Hochberg, Y., et al., "More Powerful Procedures for Multiple Significance Testing," Statistics in Medicine, 1990, 9:811-8, 8 pgs.
Hong, A., et al., "Downregulation of $GABA_A$ β Subunits is Transcriptionally Controlled by Fmr1p," J Mol Neurosci, 2012, 46:272-5, 4 pgs.
Jacquemont, S., et al., "Epigenetic Modification of the FMR1 Gene in Fragile X Syndrome Is Associated with Differential Response to the mGluR5 Antagonist AFQ056," Science Translational Medicine, 2011, vol. 3, issue 64, 11 pgs.

Kooy, R.F., et al., "Transgenic Mouse Model for the Fragile X Syndrome" Am J Med Genet, 1996, 64:241-5, 5 pgs.
Kuribara, H., et al., "Assessment of the anxiolytic and amnesic effects of three benzodiazepines, diazepam, alprazolam and triazolam, by conflict and non-matching to sample tests in mice," Nihon shinkei seishin yakurigaku zasshi = Japanese Journal of Psychopharmacology, 1997, 17(1):1-6. Abstract only, 1 pg.
Lindzey, G., et al., "Social dominance in inbred mouse strains," Nature, 1961, 191(4787):474-6. Bibliography only, 1 pg.
Liu, Z.H., et al., "Dissociation of social and nonsocial anxiety in a mouse model of fragile X syndrome," Neuroscience Letters, 2009, 454(1):62-6, 9 pgs.
Lozano, R, et al., "Fragile X syndrome: A review of clinical management," Intractable & Rare Dis Res, 2016, 5:145-157, 13 pgs.
Mientjes, E.J., et al., "The generation of a conditional Fmr1 knock out mouse model to study Fmrp function in vivo," Neurobiology of Disease, 2006, 21:549-55, 7 pgs.
Moon, J., et al., "Attentional Dysfunction, Impulsivity, and Resistance to Change in a Mouse Model of Fragile X Syndrome," Behavioral Neuroscience, 2006, 120(6):1367-79, 13 pgs.
Olmos-Serrano, J.L., et al., "The $GABA_A$ Receptor Agonist THIP Ameliorates Specific Behavioral Deficits in the Mouse Model of Fragile X Syndrome," Developmental Neuroscience, 2011, 33:395-403, 9 pgs.
Olmos-Serrano, J.L., et al., "Defective GABAergic Neurotransmission and Pharmacological Rescue of Neuronal Hyperexcitability in the Amygdala in a mouse Model of Fragile X Syndrome," The Journal of Neuroscience, 2010, 30(29):9929-38, 10 pgs.
Romero-Zerbo, Y., et al., "Protective effects of melatonin against oxidative stress in Fmr1 knockout mice: a therapeutic research model for the fragile X syndrome," Journal of Pineal Research, 2009, 46:224-34, 11 pgs.
Rudolph, U., et al., "Beyond classical benzodiazepines: Novel therapeutic potential of $GABA_A$ receptor subtypes," Nature Reviews Drug Discovety, 2011, 10(9):685-97, 26 pgs.
Schaefer, T.L., et al., "Targeted Mutations in the Na,K-ATPase Alpha 2 Isoform Confer Ouabain Resistance and Result in Abnormal Behavior in Mice," Synapse, 2011, 65:520-31, 12 pgs.
Schaefer, T.L., et al., "Mouse Pet-1 knock-out induced 5-HT disruption results in a lack of cognitive deficits and an anxiety phenotype complicated by hypoactivity and defensiveness," Neuroscience, 2009, 164(4):1431-43, 23 pgs.
Shanahan, M., et al., "Early temperament and negative reactivity in boys with fragile X syndrome," J Intellect Disabil Res, 2008, 52(part 10):842-54, 13 pgs.
Shimono, K., et al., "Long-term Recording of LTP in Cultured Hippocampal Slices," Neural Plasticity, 2002, 9(4):249-54, 6 pgs.
Sholl, D.A., *The Organization of the Cerebral Cortex*, London: Methuen & Co., 1956, 6 pgs.
Skelton, M.R., et al., "Creatine Transporter (CrT; Slc6a8) Knockout Mice as a Model of Human CrT Deficiency," PLoS One, 2011, 6(1):e16187, 11 pgs.
Sobesky, W.E., et al., "Emotional and neurocognitive deficits in fragile X," Am J Med Genet, 1994, 51:378-85, 8 pgs.
Spencer, C.M., et al., "Altered anxiety-related and social behaviors in the Fmr1 knockout mouse model of fragile X syndrome," Genes Brain Behav, 2005, 4:420-30, 11 pgs.
Thomas, A., et al., "Marble burying reflects a repetitive and perseverative behavior more than novelty-induced anxiety," Psychopharmacology (Berl), 2009, 204(2):361-73, 22 pgs.
Thomas, A.M., et al., "Group 1 metabotropic glutamate receptor antagonists alter select behaviors in a mouse model for fragile X syndrome," Psychopharmacology, 2012, 219:47-58, 13 pgs.
Tranfaglia, M.R., "Fragile X Syndrome: A Psychiatric Perspective," Chapter 16, *Results Probl Cell Differ*, 2012, 54:281-95, 16 pgs.
Tsiouris, J., et al., "Neuropsychiatric Symptoms of Fragile X Syndrome," CNS Drugs, 2004, 18(11):687-703, 17 pgs.
Veeraragavan, S., "Genetic reduction of muscarinic $M_4$ receptor modulates analgesic response and acoustic startle response in a mouse model of fragile X syndrome (FXS)," Behavioural Brain Research, 2012, 228(1):1-8, 22 pgs.

(56) References Cited

OTHER PUBLICATIONS

Williams, M.T., et al., "Neonatal methamphetamine administration induces region-specific long-term neuronal morphological changes in the rat hippocampus, nucleus accumbens and parietal cortex," The European Journal of Neuroscience, 2004, 19:3165-70, 6 pgs.

Zhou, D., et al., "A clinical study to assess CYP1A2 and CYP3A4 induction by AZD7325, a selective $GABA_A$ receptor modulator—an in vitro and in vivo comparison," Br J Clin Pharmacol, 2012, 74(1):98-108, 11 pgs.

\* cited by examiner

* Diff from WT+VEH; # Diff from KO+VEH

COMPOSITIONS AND METHODS FOR TREATMENT OF FRAGILE X SYNDROME

This application claims the benefit of U.S. application Ser. No. 14/994,705 filed Jan. 13, 2016, which claims the benefit of U.S. Application Ser. No. 62/103,126, filed Jan. 14, 2015, both of which are incorporated herein by reference it their entirety for all purposes.

BACKGROUND

Fragile X Syndrome (FXS) is the most common inherited form of developmental disability (DD), affecting 1 in 4,000 persons and is responsible for up to 2-6% of all cases of DD. FXS is also a common single gene cause of autism spectrum disorder (ASD).

BRIEF SUMMARY

Disclosed are methods of alleviating or preventing one or more symptoms associated with fragile X syndrome in an individual in need thereof via administration of a therapeutically effective amount of a GABA(A) alpha 2 and/or 3 partial agonist. The one or more symptoms may include impaired social and functional communication, anxiety, inattention, hyperactivity, altered sensory reactivity, self-injury, aggression, impaired cognitive function, compromised daily living skills, or a combination thereof.

BRIEF DESCRIPTION OF THE DRAWINGS

FIG. 4; top main effect of genotype ($P<0.001$) and drug ($P<0.0001$) for Vmax) shows that Fmr1 KO mice treated chronically with the low dose of AZD7325 have significantly reduced whole body flinching in this low-level Acoustic startle paradigm. Interestingly, in a paradigm employing a high level acoustic stimulus (120 dB), adult Fmr1 KO mice will repeatedly respond to the stimulus with a lower amplitude whole body flinch compared to WT mice. FIG. 4; bottom (Gene×Drug interaction $P<0.0001$) shows that treatment with AZD7325 improves this response to WT levels demonstrating that drug treatment isn't simply reducing overall whole body flinching in response to sensory stimuli, but is rather mediating responses so that they are becoming more appropriate and reflective of startle intensity. *P indicates significantly different from WT+VEH; #P indicates significantly different from KO+VEH.

DETAILED DESCRIPTION

Figure 1:
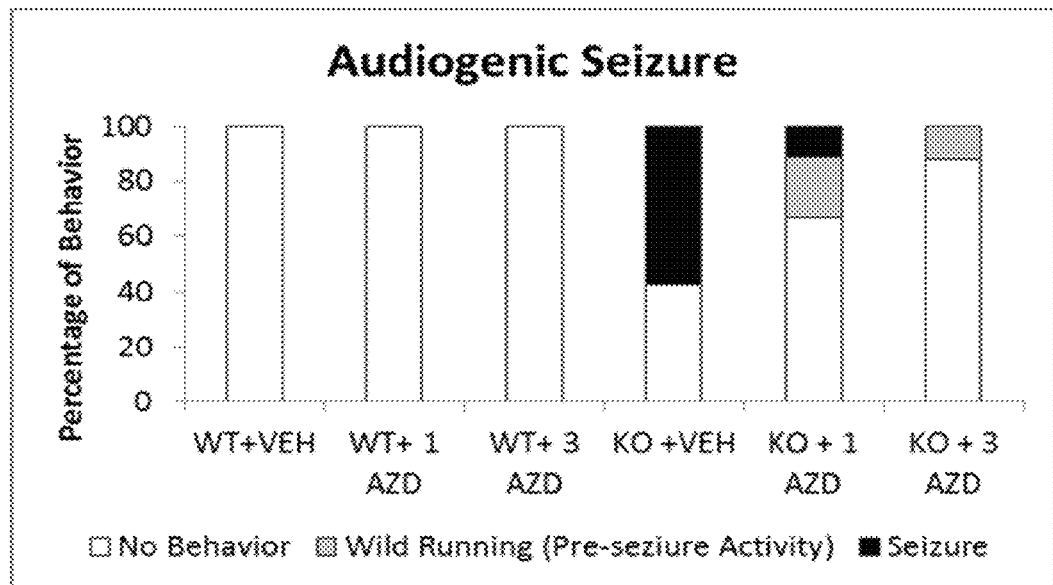
FIG. 1 shows that approximately 60% Fmr1 KO mice treated with VEH displayed wild running followed by seizure in response to a loud stimulus (120 dB siren), but when treated acutely (30 min prior to testing) with both the low (11%) and high (0%) dose of 4-amino-8-(2-fluoro-6-methoxy-phenyl)-N-propyl-cinnoline-3-carboxamide ("AZD7325"), seizure activity was significantly reduced, indicating that the drug is reducing hyperexcitability in the brain (Fisher's exact test $p<0.0002$).

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviations, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

"Dosage unit form" as used herein refers to physically discrete units suited as unitary dosages for the subject to be treated, each unit containing a predetermined quantity of active compound calculated to produce the desired therapeutic effect in association with the required pharmaceutical carrier. The specification for the dosage unit forms of the preferred embodiments are dictated by and directly dependent on the unique characteristics of the active compound and the particular therapeutic effect to be achieved, and the limitations inherent in the art of compounding such an active compound for the treatment of individuals.

The terms "individual," "host," "subject," and "patient" are used interchangeably to refer to an animal that is the object of treatment, observation and/or experiment. "Animal" includes vertebrates and invertebrates, such as fish, shellfish, reptiles, birds, and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. Pharmaceutically acceptable carriers include a wide range of known diluents (i.e., solvents), fillers, extending agents, binders, suspending agents, disintegrates, surfactants, lubricants, excipients, wetting agents and the like commonly used in this field. These carriers may be used singly or in combination according to the form of the pharmaceutical preparation, and may further encompass "pharmaceutically acceptable excipients" as defined herein.

As used herein, "pharmaceutically acceptable excipient" means any other component added to a pharmaceutical formulation other than the active ingredient and which is capable of bulking-up formulations that contain potent active ingredients (thus often referred to as "bulking agents," "fillers," or "diluents") to allow convenient and accurate dispensation of a drug substance when producing a dosage form. Excipients may be added to facilitate manufacture, enhance stability, control release, enhance product characteristics, enhance bioavailability drug absorption or solubility, or other pharmacokinetic considerations, enhance patient acceptability, etc. Pharmaceutical excipients include, for example, carriers, fillers, binders, disintegrants, lubricants, glidants, colors, preservatives, suspending agents, dispersing agents, film formers, buffer agents, pH adjusters, preservatives etc. The selection of appropriate excipients also depends upon the route of administration and the dosage form, as well as the active ingredient and other factors, and will be readily understood by one of ordinary skill in the art.

As used herein, the term "therapeutically effective amount" means the total amount of each active component of the pharmaceutical composition or method that is sufficient to show a meaningful patient benefit, e.g., healing of chronic conditions or in an increase in rate of healing of such conditions, or in a reduction in aberrant conditions. This includes both therapeutic and prophylactic treatments. Accordingly, the compounds can be used at very early stages of a disease, or before early onset, or after significant progression. When applied to an individual active ingredient, administered alone, the term refers to that ingredient alone. When applied to a combination, the term refers to combined amounts of the active ingredients that result in the therapeutic effect, whether administered in combination, serially or simultaneously.

FXS results from an expanded CGG triplet repeat expansion resulting in methylation and transcriptional silencing of the Fragile X Mental Retardation 1 gene and transcriptional silencing of the Fragile X Mental Retardation Protein (FMRP). FMRP is known to be an RNA binding protein responsible for translational control of hundreds of genes involved in various functions including, but not limited to, intracellular and synaptic signalling. Of the many genes known to be regulated by FMRP, the gamma-aminobutyric acid receptor A (GABA(A)) is gaining attention as a potential pharmacotherapy target for the treatment of FXS. Mounting evidence suggests decreased expression and functioning of GABA(A) is intimately involved in the pathophysiology of FXS. Non-selective GABA(A) agonism in animal models of FXS has been associated with the normalization of morphological features, GABA(A) expression, and some behavior. One down side of the nonselective nature of these agents is the increased likelihood of unwanted side-effects, such as sedation and dulling of cognition, which could impeded the long-term use of non-selective GABA(A) agonist pharmacotherapy in FXS. Benzodiazepines act as potent non-selective agonists across GABA(A) receptor subunits alpha 1, alpha 2, alpha 3, and alpha 5. Therefore, use of benzodiazepines is often limited in FXS given concerns over drug tolerability rooted in the sedating and potentially cognitively dulling features of this drug class. The sedating and amnesic effects of benzodiazepines are due to effects at alpha1 and alpha 5 subunit containing receptors, respectively.

Recent pre-clinical findings in Fragile X Syndrome knockout animal models have led to targeted treatment development efforts in this field. To date, drug development focused on metabotropic glutamate receptor type 5 (mGluR5) antagonists and a gamma-aminobutyric acid receptor B (GABA(B)) agonist have not been marked by a robust, universal drug effect. In both mGluR5 and GABA(B) human trials to date, only subsets of persons with FXS have potentially shown response with treatment but larger studies have failed to demonstrate efficacy over placebo. Given these finding, there is a clear need to explore unique mechanisms of treatment in this field. Increasing evidence has pointed to dysregulation of GABA(A) receptor (GABA(A)) neurotransmission in the pathophysiology of FXS. Among potential targets of drug therapy in FXS, modulation of GABA(A) activity, in particular selective agonism, remains largely unexplored in humans with FXS. Preclinical data implicating GABA(A) dysregulation in FXS includes evidence that Fragile X Mental Retardation Protein (FMRP) transcriptionally regulates GABA(A) receptor subunit RNA expression with reductions in GABA(A) receptor mRNA noted in FXS KO mice lacking FMRP, Additionally, GABA (A) receptor expression has been shown to be significantly down regulated in a number of brain regions in FXS KO mice that are important for behavior including the hippocampus and amygdala. In animal models of FXS, non-selective or extrasynaptic GABA(A) agonism has shown significant promise as a pharmacotherapy target. Regarding preclinical treatment, study of the GABA(A) agonist in FXS, alphaxalone, a neuroactive steroid with multiple potential pharmacodynamics effect including modulation of nicotinic acetylcholine receptors, activation of chloride channels, and non-selective GABA(A) agonism, was associated with reductions in anxiety and rescue of audiogenic seizures in FXS KO mice. Also in FXS KO mice, the GABA(A) extrasynaptic δ-subunit agonist gaboxadol restored neuron excitability deficits in the amygdala, reduced hyperactivity, and reduced prepulse inhibition (PPI) alterations. No studies published to date have assessed GABA(A) modulation via a specific alpha 2,3 partial agonist.

Given the limitations in available FDA approved GABA (A) focused treatments of FXS, Applicant has investigated a novel selective GABA(A) agonist in a mouse model of FXS. In one aspect, the novel agonist is a specific GABA(A) alpha2,3, partial agonist. In a further aspect, the compound is 4-amino-8-(2-fluoro-6-methoxy-phenyl)-N-propyl-cinnoline-3-carboxamide ("AZD7325"). Applicant has shown that, using the disclosed partial agonist, several key behavioral deficits in the Fmr1 KO mouse model are normalized or attenuated.

In one aspect, a method of alleviating or preventing one or more signs or symptoms of fragile X is disclosed. The method may comprise the step of administering to a subject in need thereof, a therapeutically effective amount of a GABA(A) alpha 2 and/or 3 partial agonist.

In one aspect, the GABA(A) alpha 2 and/or 3 agonist or partial agonist may act at the GABA(A) receptor site, and may have a lower binding affinity to and/or less efficacy of receptor activation at the GABA(A) alpha 1 subunit as compared to the binding affinity and/or receptor efficacy at the alpha 2 and/or alpha 3 subunit.

In one aspect, the GABA(A) alpha 2,3 agonist may be selected from

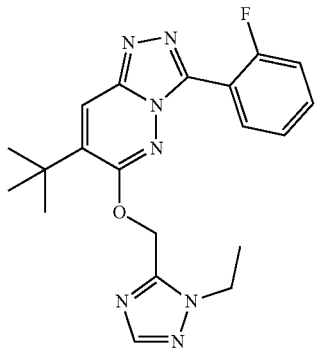

(TPA-023)

or a pharmaceutically acceptable salt thereof;

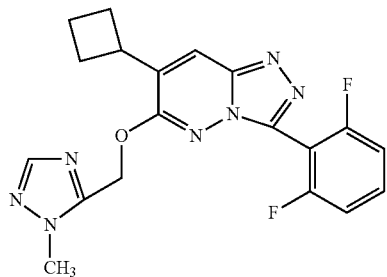

(MK-0343)

or a pharmaceutically acceptable salt thereof;

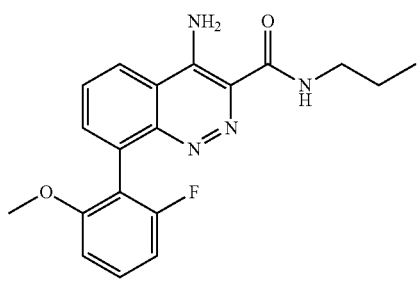 [SMILES: CCCNC(=O)c1nnc2c(-c3c(F)cccc3OC)cccc2c1N]

(4-amino-8-(2-fluoro-6-methoxy-phenyl)-N-propyl-cinnoline-3-carboxamide) or a pharmaceutically acceptable salt thereof;

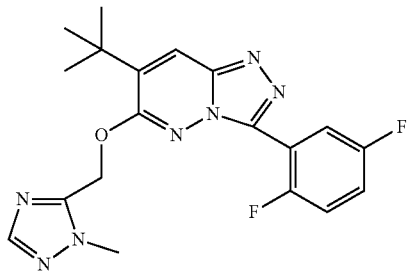 [SMILES: Cn1ncnc1COc1nn2c(-c3cc(F)ccc3F)nnc2cc1C(C)(C)C]

3-(2,5-Difluorophenyl)-7-(1,1-dimethylethyl)-6-[(1-methyl-1H-1,2,4-triazo-1-5-yl)methoxy]-1,2,4-triazolo[4,3-b]pyridazine or a pharmaceutically acceptable salt thereof; or combinations thereof.

In a further aspect, the compound may be a compound having alpha 2 and/or 3, partial agonist activity as described in WO1999037303 and/or U.S. Pat. No. 6,399,608 entitled "Combination of a GABA-A Alpha 2/3 agonist and a Selective Serotonin Reuptake Inhibitor" published Jul. 29, 1999).

In one aspect, the one or more signs and symptoms may be selected from impaired functional communication, anxiety, inattention, hyperactivity, sensory reactivity, autonomic nervous system dysregulation, aberrant eye gaze, self injury, aggression, seizures, EEG abnormalities including but not limited to abnormal spectral analysis, event related potentials which may include auditory and visual responses, abnormalities in cortical responses as evoked by transcranial magnetic stimulation including resting and active motor thresholds and abnormal responses in measures of cortical inhibition and excitation, aberrant impaired cognitive function, compromised daily living skills, or a combination thereof.

In one aspect, the GABA(A) alpha 2 and/or 3 partial agonist may be co-administered with co-administered with an agent selected from an atypical antipsychotics, lithium, a selective serotonin reuptake inhibitor (SSRI), a serotonin noradrenergic reuptake inhibitor (SNRI), non-SSRI non-SNRI serotonergic drug, a benzodiazepine, a glutamatergic drug, a GABA(B) modulator, opiate receptor modulators, endocannabinoid system modulators, a medication for the treatment of attention deficit hyperactivity disorder (ADHD), anti-epileptics, alpha 2-agonists, or a combination thereof.

In one aspect, the GABA(A) alpha 2 and/or 3 partial agonist may be co-administered with an agent selected from oxytocin, lithium, minocycline, or a combination thereof.

In one aspect, the GABA(A) alpha 2 and/or 3 partial agonist may be co-administered with structured non-drug therapies including occupational therapy, speech therapy, language learning interventions, social skills training, cognitive behavioral therapy, discrete trial training, biofeedback, computerized cognitive training, or a combination thereof.

In one aspect, the GABA(A) alpha 2 and/or 3 partial agonist may be administered in a dose of from about 2 g bid to about 15 g bid, or about 5 g bid to about 10 g bid.

In one aspect, the administration step may be carried out until ERK phosphorylation is normalized. The ERK phosphorylation normalization may be determined via measurement in the blood of a subject receiving said GABA(A) alpha 2 and/or 3 partial agonist.

Compositions

Compounds, or mixtures of compounds described herein, can be formulated into pharmaceutical composition comprising a pharmaceutically acceptable carrier and other excipients as apparent to the skilled worker. Such composition can additionally contain effective amounts of other compounds, especially for the treatment of conditions, diseases, and/or disorders described herein.

Some embodiments comprise the administration of a pharmaceutically effective quantity of active agent or its pharmaceutically acceptable salts or esters, active agent analogs or their pharmaceutically acceptable salts or esters, or a combination thereof.

The compositions and preparations may contain at least 0.1% of active agent. The percentage of the compositions and preparations can, of course, be varied, and can contain between about 2% and 60% of the weight of the amount administered. The percentage of the compositions and preparations may contain between about 2, 5, 10, or 15% and 30, 35, 40, 45, 50, 55, or 60% of the weight of the amount administered. The amount of active compounds in such pharmaceutically useful compositions and preparations is such that a suitable dosage will be obtained.

The disclosed active agents may form salts. Reference to a compound of the active agent herein is understood to include reference to salts thereof, unless otherwise indicated. The term "salt(s)", as employed herein, denotes acidic and/or basic salts formed with inorganic and/or organic acids and bases. In addition, when an active agent contains both a basic moiety, such as, but not limited to an amine or a pyridine or imidazole ring, and an acidic moiety, such as, but not limited to a carboxylic acid, zwitterions ("inner salts") can be formed and are included within the term "salt(s)" as used herein. Pharmaceutically acceptable (e.g., non-toxic, physiologically acceptable) salts are preferred, although other salts are also useful, e.g., in isolation or purification steps, which can be employed during preparation. Salts of the compounds of the active agent can be formed, for example, by reacting a compound of the active agent with an amount of acid or base, such as an equivalent amount, in a medium such as one in which the salt precipitates or in an aqueous medium followed by lyophilization.

Pharmaceutically acceptable salts include, but are not limited to, pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

The compounds can be formulated in various forms, including solid and liquid forms, such as tablets, gel, syrup, powder, aerosol, etc.

The compositions may contain physiologically acceptable diluents, fillers, lubricants, excipients, solvents, binders, stabilizers, and the like. Diluents that can be used in the compositions include but are not limited to dicalcium phosphate, calcium sulphate, lactose, cellulose, kaolin, mannitol, sodium chloride, dry starch, powdered sugar and for prolonged release tablet-hydroxy propyl methyl cellulose (HPMC). The binders that can be used in the compositions include but are not limited to starch, gelatin and fillers such as sucrose, glucose, dextrose and lactose.

Natural and synthetic gums that can be used in the compositions include but are not limited to sodium alginate, ghatti gum, carboxymethyl cellulose, methyl cellulose, polyvinyl pyrrolidone and veegum. Excipients that can be used in the compositions include but are not limited to microcrystalline cellulose, calcium sulfate, dicalcium phosphate, starch, magnesium stearate, lactose, and sucrose. Stabilizers that can be used include but are not limited to polysaccharides such as acacia, agar, alginic acid, guar gum and tragacanth, amphotsics such as gelatin and synthetic and semi-synthetic polymers such as carbomer resins, cellulose ethers and carboxymethyl chitin.

Solvents that can be used include but are not limited to Ringers solution, water, distilled water, dimethyl sulfoxide to 50% in water, propylene glycol (neat or in water), phosphate buffered saline, balanced salt solution, glycol and other conventional fluids.

The dosages and dosage regimen in which the compounds are administered will vary according to the dosage form, mode of administration, the condition being treated and particulars of the patient being treated. Accordingly, optimal therapeutic concentrations will be best determined at the time and place through routine experimentation.

The compounds may also be used enterally. Orally, the compounds may be administered at the rate of 100 µg to 100 mg per day per kg of body weight. Orally, the compounds may be suitably administered at the rate of about 100, 150, 200, 250, 300, 350, 400, 450, or 500 µg to about 1, 5, 10, 25, 50, 75, 100 mg per day per kg of body weight. The required dose can be administered in one or more portions. For oral administration, suitable forms are, for example, tablets, gel, aerosols, pills, dragees, syrups, suspensions, emulsions, solutions, powders and granules; one method of administration includes using a suitable form containing from 1 mg to about 500 mg of active substance. In one aspect, administration may comprise using a suitable form containing from about 1, 2, 5, 10, 25, or 50 mg to about 100, 200, 300, 400, 500 mg of active substance.

The compounds may also be administered parenterally in the form of solutions or suspensions for intravenous or intramuscular perfusions or injections. In that case, the compounds may be administered at the rate of about 10 µg to 10 mg per day per kg of body weight; one method of administration may consist of using solutions or suspensions containing approximately from 0.01 mg to 1 mg of active substance per ml. The compounds may be administered at the rate of about 10, 20, 30, 40, 50, 60, 70, 80, 90, or 100 µg to 1, 2, 3, 4, 5, 6, 7, 8, 9, or 10 mg per day per kg of body weight; in one aspect, solutions or suspensions containing approximately from 0.01, 0.02, 0.03, 0.04, or 0.5 mg to 0.1, 0.2, 0.3, 0.4, 0.5, 0.6, 0.7, 0.8, 0.9, or 1 mg of active substance per ml may be used.

The active compounds and/or pharmaceutical compositions of the embodiments disclosed herein can be administered according to various routes, such as by injection, for example local or systemic injection(s). Intratumoral injections maybe used. Other administration routes can be used as well, such as intramuscular, intravenous, intradermic, subcutaneous, etc. Furthermore, repeated injections can be performed, if needed, although it is believed that limited injections will be needed in view of the efficacy of the compounds.

For ex vivo administration, the active agent can be administered by any standard method that would maintain viability of the cells, such as by adding it to culture medium (appropriate for the target cells) and adding this medium directly to the cells. As is known in the art, any medium used in this method can be aqueous and non-toxic so as not to render the cells non-viable. In addition, it can contain standard nutrients for maintaining viability of cells, if desired. For in vivo administration, the complex can be added to, for example, to a pharmaceutically acceptable carrier, e.g., saline and buffered saline, and administered by any of several means known in the art. Examples of administration include parenteral administration, e.g., by intravenous injection including regional perfusion through a blood vessel supplying the tissues(s) or organ(s) having the target cell(s), or by inhalation of an aerosol, subcutaneous or intramuscular injection, topical administration such as to skin wounds and lesions, direct transfection into, e.g., bone marrow cells prepared for transplantation and subsequent transplantation into the subject, and direct transfection into an organ that is subsequently transplanted into the subject. Further administration methods include oral administration, particularly when the active agent is encapsulated, or rectal administration, particularly when the active agent is in suppository form.

It is contemplated that such target cells can be located within a subject or human patient, in which case a safe and effective amount of the active agent, in pharmacologically acceptable form, would be administered to the patient. Generally speaking, it is contemplated that useful pharmaceutical compositions may include the selected active compound derivative in a convenient amount, e.g., from about 0.001% to about 10% (w/w) that is diluted in a pharmacologically or physiologically acceptable carrier, such as, for example, phosphate buffered saline. The route of administration and ultimate amount of material that is administered to the subject under such circumstances will depend upon the intended application and will be apparent to those of skill in the art in light of the examples which follow.

Any composition chosen should be of low or non-toxicity to the cell. Toxicity for any given compound can vary with the concentration of compound used. It is also beneficial if the compound chosen is metabolized or eliminated by the body and if this metabolism or elimination is done in a manner that will not be harmfully toxic.

The compound may be administered such that a therapeutically effective concentration of the compound is in contact with the affected cells of the body. The dose administered to a subject, particularly a human, may be sufficient to effect a therapeutic response in the subject over a reasonable period of time. The dose may be determined by the strength of the particular compound employed and the condition of the subject, as well as the body weight of the subject to be treated. The existence, nature, and extent of any adverse side effects that might accompany the administration of a particular compound also will determine the size of the dose and the particular route of administration employed with a particular patient. In general, the compounds may be therapeutically effective at low doses. The generally useful dose range may be from about 0.001 mM, or less, to about 100 mM, or more. The effective dose range may be from about 0.01, 0.05, 0.1, 0.5, 0.6, 0.7, 0.8, or 0.9 mM, to about 1, 2, 3, 4, 5, 6, 7, 8, 9, or 10 mM. Accordingly, the compounds may be generally administered in low doses.

The pharmaceutical composition may further comprise a pharmaceutically acceptable carrier. The resulting preparation may incorporate, if necessary, one or more solubilizing agent, buffers, preservatives, colorants, perfumes, flavorings and the like that are widely used in the field of pharmaceutical preparation.

The proportion of the active ingredient to be contained in the disclosed compositions may be determined by one of ordinary skill in the art using art recognized methods.

The disclosed compounds may be formulated into a dosage form selected from the group consisting of tablets, capsules, granules, pills, injections, solutions, emulsions, suspensions, and syrups. The form and administration route for the pharmaceutical composition are not limited and can be suitably selected. For example, tablets, capsules, granules, pills, syrups, solutions, emulsions, and suspensions may be administered orally. Additionally, injections (e.g. subcutaneous, intravenous, intramuscular, and intraperitoneal) may be administered intravenously either singly or in combination with a conventional replenisher containing glucose, amino acid and/or the like, or may be singly administered intramuscularly, intracutaneously, subcutaneously and/or intraperitoneally.

The disclosed compositions may be prepared according to a method known in the pharmaceutical field of this kind using a pharmaceutically acceptable carrier. For example, oral forms such as tablets, capsules, granules, pills and the like are prepared according to known methods using excipients such as saccharose, lactose, glucose, starch, mannitol and the like; binders such as syrup, gum arabic, sorbitol, tragacanth, methylcellulose, polyvinylpyrrolidone and the like; disintegrates such as starch, carboxymethylcellulose or the calcium salt thereof, microcrystalline cellulose, polyethylene glycol and the like; lubricants such as talc, magnesium stearate, calcium stearate, silica and the like; and wetting agents such as sodium laurate, glycerol and the like.

Injections, solutions, emulsions, suspensions, syrups and the like may be prepared according to a known method suitably using solvents for dissolving the active ingredient, such as ethyl alcohol, isopropyl alcohol, propylene glycol, 1,3-butylene glycol, polyethylene glycol, sesame oil and the like; surfactants such as sorbitan fatty acid ester, polyoxyethylenesorbitan fatty acid ester, polyoxyethylene fatty acid ester, polyoxyethylene of hydrogenated castor oil, lecithin and the like; suspending agents such as cellulose derivatives including carboxymethylcellulose sodium, methylcellulose and the like, natural gums including tragacanth, gum arabic and the like; and preservatives such as parahydroxybenzoic acid esters, benzalkonium chloride, sorbic acid salts and the like.

The compounds can be administered orally, topically, parenterally, by inhalation or spray, vaginally, rectally, nasally, or sublingually. The compounds may be administered in dosage unit formulations. The term "administration by injection" includes but is not limited to: intravenous, intraarticular, intramuscular, subcutaneous and parenteral injections, as well as use of infusion techniques. Dermal administration can include topical application or transdermal administration. One or more compounds can be present in association with one or more non-toxic pharmaceutically acceptable carriers and if desired other active ingredients.

Compositions intended for oral use can be prepared according to any suitable method known to the art for the manufacture of pharmaceutical compositions. Such compositions can contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients that are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets can be uncoated or they can be coated by known techniques to delay disintegration and adsorption in the gastrointestinal tract and thereby provide a sustained action over a longer period. For example, a time delay material such as glyceryl monostearate or glyceryl distearate can be employed. These compounds can also be prepared in solid, rapidly released form.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions can also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, can also be present.

The compounds can also be in the form of non-aqueous liquid formulations, e.g., oily suspensions which can be formulated by suspending the active ingredients in a vegetable oil, for example arachis oil, olive oil, sesame oil or peanut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide palatable oral preparations. These compositions can be preserved by the addition of an anti-oxidant such as ascorbic acid.

Compounds may also be administered transdermally using methods known to those skilled in the art. For example, a solution or suspension of an active agent in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of an active agent can be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents can also include mixtures of one or more materials selected from lower alcohols, lower ketones, lower carboxylic acid esters, polar ethers, lower hydrocarbons, halogenated hydrocarbons.

Suitable penetration enhancing materials for transdermal delivery system are known to those skilled in the art, and include, for example, monohydroxy or polyhydroxy alcohols such as ethanol, propylene glycol or benzyl alcohol, saturated or unsaturated C8-C18 fatty alcohols such as lauryl alcohol or cetyl alcohol, saturated or unsaturated C8-C18 fatty acids such as stearic acid, saturated or unsaturated fatty esters with up to 24 carbons such as methyl, ethyl, propyl, isopropyl, n-butyl, sec-butyl, isobutyl, tertbutyl or monoglycerin esters of acetic acid, capronic acid, lauric acid, myristinic acid, stearic acid, or palmitic acid, or diesters of saturated or unsaturated dicarboxylic acids with a total of up to about 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations can also include mixtures of one or more materials selected from monohydroxy or polyhydroxy alcohols, saturated or unsaturated C8-C18 fatty alcohols, saturated or unsaturated C8-C18 fatty acids, saturated or unsaturated fatty esters with up to 24 carbons, diesters of saturated or unsaturated discarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrenebutadiene copolymers, and natural and synthetic rubbers. Cellulose ethers, derivatized polyethylenes, and silicates can also be used as matrix components. Additional additives, such as viscous resins or oils can be added to increase the viscosity of the matrix.

Pharmaceutical compositions may also be in the form of oil-in-water emulsions. The oil phase can be a vegetable oil, for example olive oil or arachis oil, or a mineral oil, for example, liquid paraffin or mixtures of these. Suitable emulsifying agents can be naturally-occurring gums, for example, gum acacia or gum tragacanth, naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions can also contain sweetening and flavoring agents. Syrups and elixirs can be formulated with sweetening agents, for example glycerol, propylene glycol, sorbitol or sucrose. Such formulations can also contain a demulcent, a preservative and flavoring and coloring agents.

The compounds can also be administered in the form of suppositories for rectal or vaginal administration of the drug. These compositions can be prepared by mixing the drug with a suitable nonirritating excipient which is solid at ordinary temperatures but liquid at the rectal temperature or vaginal temperature and will therefore melt in the rectum or vagina to release the drug. Such materials include cocoa butter and polyethylene glycols.

The compositions may be further administered intranasally. In such aspect, the compositions may further comprise other agents suited for improved delivery across nasal mucosa. For example, in certain aspects, agents such as a permeation enhancer, a polymer capable of increasing mucosal adhesion of the composition, or a combination thereof may be included in the composition.

It will be appreciated by those skilled in the art that the particular method of administration will depend on a variety of factors, all of which are considered routinely when administering therapeutics. It will also be understood, however, that the specific dose level for any given patient will depend upon a variety of factors, including, the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, i.e., the mode of treatment and the daily number of doses of an active agent or a pharmaceutically acceptable salt thereof given for a defined number of days, can be ascertained by those skilled in the art using conventional treatment tests.

EXAMPLES

As a validated model of FXS, Fmr1 KO mice exhibit altered responses to sensory stimuli (auditory, pain, etc.), and learning impairments. Additionally they also exhibit aberrant ERK1/2 activation along with abnormal dendritic spines and altered synaptic plasticity. AZD7325, 4-amino-8-(2-fluoro-6-methoxy-phenyl)-N-propyl-cinnoline-3-carboxamide, is a potent selective partial GABA(A) α2,3 receptor agonist developed by AstraZeneca (AZ) for the treatment of anxiety, having the following structure:

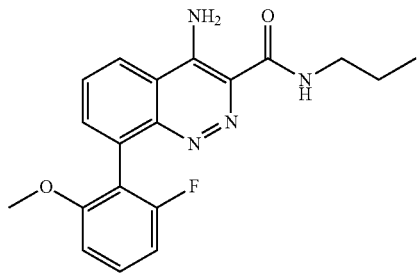 [SMILES: CCCNC(=O)c1nnc2c(-c3c(F)cccc3OC)cccc2c1N]

Throughout experiments in Fmr1 KO mice, we treated animals with 1 mg/kg AZD7325, 3 mg/kg AZD7325 or vehicle (VEH) by oral gavage to mimic the human exposure route. Juvenile mice were treated acutely and adult mice were treated chronically prior to and throughout behavior analysis. Data were analyzed by 2-way ANOVA unless otherwise indicated. *p≤0.05 indicates significantly different than WT+VEH group.

Figure 2:
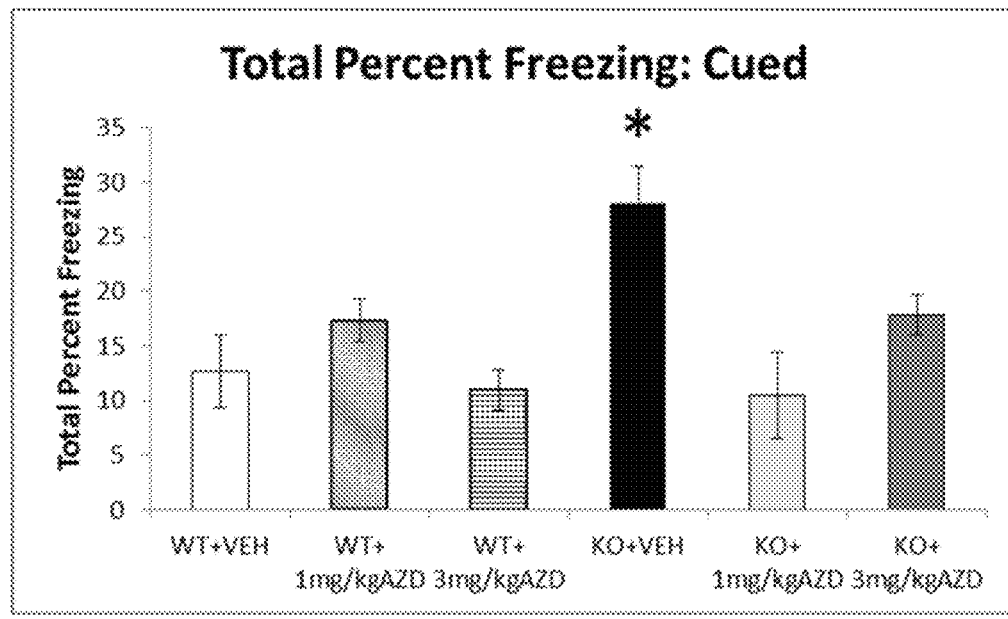
FIG. 2 shows that the conditioned fear responses to a mild foot shock were shown to be exaggerated in Fragile X Syndrome KO mice compared to WT mice during the cued portion of the test with 4-amino-8-(2-fluoro-6-methoxy-phenyl)-N-propyl-cinnoline-3-carboxamide ("AZD7325") treatment at both dose levels normalizing this behavior in KO mice.
Figure 3:
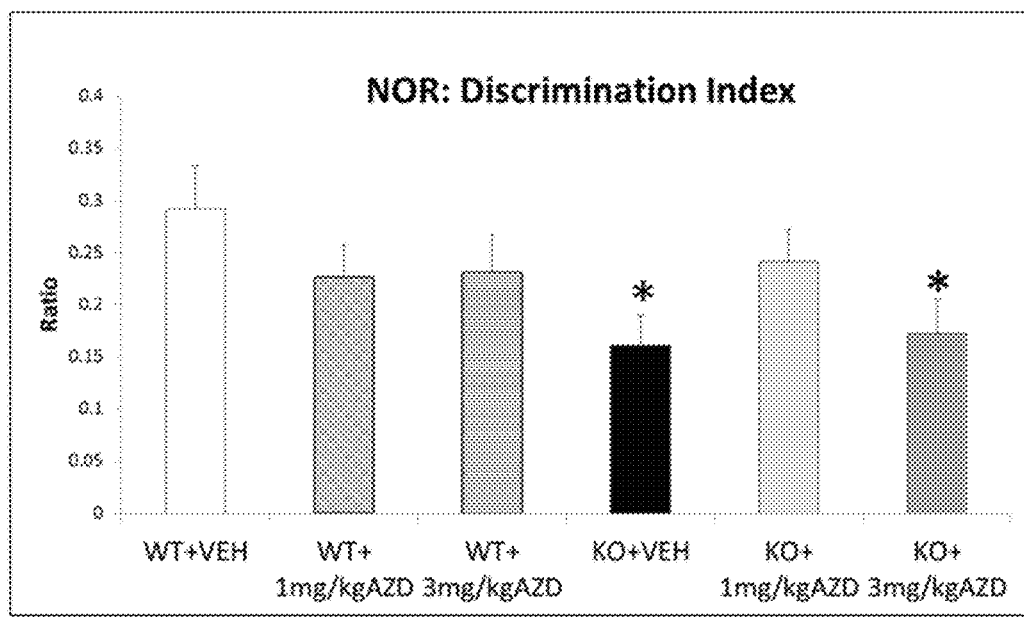
FIG. 3 shows the results of treatment with low dose AZD7325 improves memory in Fragile X Syndrome KO mice. Such treatment attenuates deficits in object memory when assessed in a novel object recognition paradigm indicated by an increase in discrimination index ratio (DI) in the low dose KO mice (FIG. 3; main effect of genotype for discrimination index ($F(1,86)=4.99$, $P<0.03$)).
Figure 4:
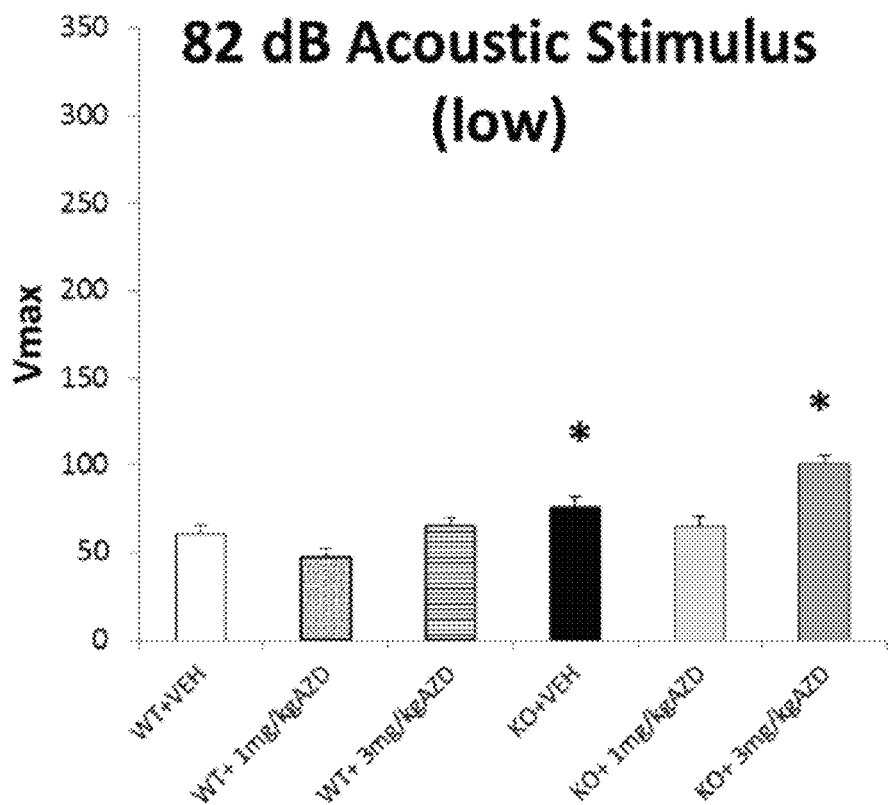
FIG. 4 shows that the response to acoustic stimuli in KO mice is corrected and response to intensity is appropriately gated with AZD7325 treatment. In adulthood, Fmr1 KO mice have abnormal motor responses to sensory stimuli compared to WT mice in an acoustic startle paradigm. When presented with a short low level white noise burst (82 db) over 10 trial blocks, Fmr1 KO mice will flinch at a higher amplitude than WT mice (presentation of these startle bursts do not elicit seizure activity).
Figure 4:
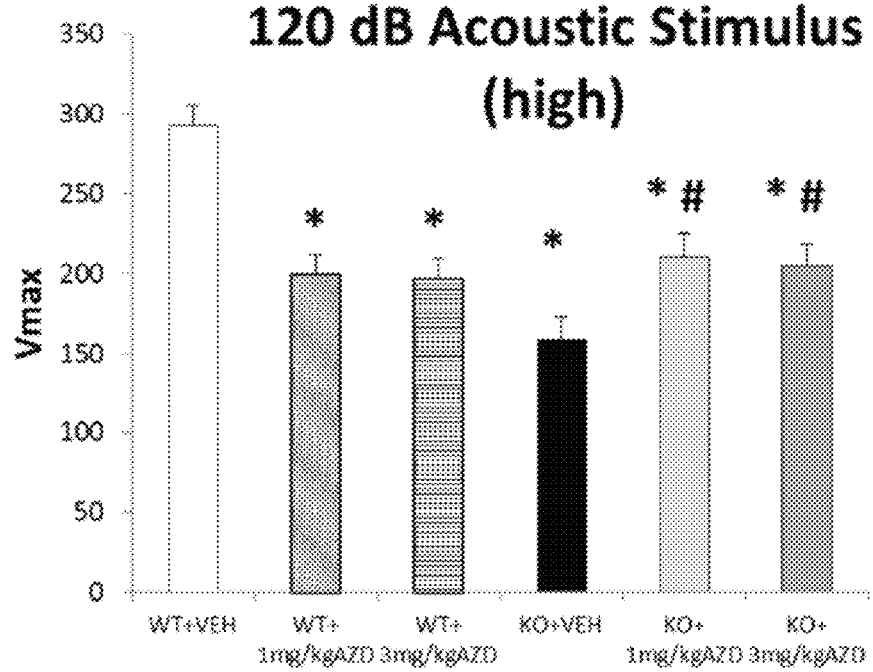

Audiogenic seizure susceptibility in Fmr1 KO mice, which is thought to be the result of increased neuronal activity in response to sensory stimuli, peaks around the third week of life and manifests as wild running which is typically followed by tonic-clonic seizure. WT mice do not respond to this siren with any noticeable running or seizure behavior. FIG. 1 shows that approximately 60% Fmr1 KO mice treated with VEH displayed wild running followed by seizure in response to a loud stimulus (120 dB siren), but when treated acutely (30 min prior to testing) with both the low (11%) and high (0%) dose of 4-amino-8-(2-fluoro-6-methoxy-phenyl)-N-propyl-cinnoline-3-carboxamide, seizure activity was significantly reduced, indicating that the drug is reducing hyperexcitability in the brain (Fisher's exact test p<0.0002). In adulthood, Fmr1 KO mice have abnormal motor responses to sensory stimuli compared to WT mice in an acoustic startle paradigm. When presented with a short low level white noise burst (82 db) over 10 trial blocks, Fmr1 KO mice will flinch at a higher amplitude than WT mice (presentation of these startle bursts do not elicit seizure activity). FIG. 4; top main effect of genotype (P<0.001) and drug (P<0.0001) for Vmax) shows that Fmr1 KO mice treated chronically with the low dose of AZD7325 have significantly reduced whole body flinching in this low-level Acoustic startle paradigm. Interestingly, in a paradigm employing a high level acoustic stimulus (120 dB), adult Fmr1 KO mice will repeatedly respond to the stimulus with a lower amplitude whole body flinch compared to WT mice. FIG. 4; bottom (Gene×Drug interaction P<0.0001) shows that treatment with AZD7325 improves this response to WT levels demonstrating that drug treatment isn't simply reducing overall whole body flinching in response to sensory stimuli, but is rather mediating responses so that they are becoming more appropriate and reflective of startle intensity. *P indicates significantly different from WT+VEH; #P indicates significantly different from KO+VEH. Conditioned fear responses to a mild foot shock were shown to be exaggerated compared to WT mice during the cued portion of the test with 4-amino-8-(2-fluoro-6-methoxy-phenyl)-N-propyl-cinnoline-3-carboxamide treatment at both dose levels normalizing this behavior in KO mice (FIG. 2; main effect of genotype (F(1,20)=4.26, P<0.05), and gene×drug interaction (F(2,20)=7.79, P<0.003)). This type of deficit in the VEH-treated Fmr1 KO mice is reminiscent of the exaggerated anxiety responses people with FXS commonly display. Treatment with the low dose of 4-amino-8-(2-fluoro-6-methoxy-phenyl)-N-propyl-cinnoline-3-carboxamide also attenuates deficits in object memory when assessed in a novel object recognition paradigm (FIG. 3; main effect of genotype for discrimination index (F(1,86)=4.99, P<0.03)).

Low dose-treated animals showed greater interest in the novel object during the second phase compared to VEH-treated KO mice indicating a greater memory of the familiar object which was introduced during the first phase of the test. Based upon preclinical data in FXS implicating insufficient GABA(A) activity in the pathophysiology of the disorder combined with preclinical and human evidence (unpublished data) supporting the tolerability and effectiveness of improving aberrant behavior, 4-amino-8-(2-fluoro-6-methoxy-phenyl)-N-propyl-cinnoline-3-carboxamide is an ideal molecule to develop as a clinical treatment in humans with FXS.

REFERENCES

1. D'Hulst C, De Geest N, Reeve S P, et al. Decreased expression of the GABAA receptor in fragile X syndrome. Brain research 2006; 1121:238-45.
2. D'Hulst C, Kooy R F. The GABAA receptor: a novel target for treatment of fragile X? Trends in neurosciences 2007; 30:425-31.

3. Olmos-Serrano J L, Corbin J G, Burns M P. The GABA (A) receptor agonist THIP ameliorates specific behavioral deficits in the mouse model of fragile X syndrome. Developmental neuroscience 2011; 33:395-403.
4. Olmos-Serrano J L, Paluszkiewicz S M, Martin B S, Kaufmann W E, Corbin J G, Huntsman M M. Defective GABAergic neurotransmission and pharmacological rescue of neuronal hyperexcitability in the amygdala in a mouse model of fragile X syndrome. The Journal of neuroscience: the official journal of the Society for Neuroscience 2010; 30:9929-38.
5. Heulens I, D'Hulst C, Van Dam D, De Deyn P P, Kooy R F. Pharmacological treatment of fragile X syndrome with GABAergic drugs in a knockout mouse model. Behavioural brain research 2012; 229:244-9.
6. Jacquemont S, Curie A, des Portes V, et al. Epigenetic modification of the FMR1 gene in fragile X syndrome is associated with differential response to the mGluR5 antagonist AFQ056. Science translational medicine 2011; 3:64ra1.
7. Berry-Kravis E M, Hessl D, Rathmell B, et al. Effects of STX209 (Arbaclofen) on Neurobehavioral Function in Children and Adults with Fragile X Syndrome: A Randomized, Controlled, Phase 2 Trial. Sci Transl Med 2012; 4:152ra27.
8. Heulens I, D'Hulst C, Braat S, Rooms L, Kooy R F. Involvement and therapeutic potential of the GABAergic system in the fragile X syndrome. Scientific World Journal 2010; 10:2198-206.
9. Hong A, Zhang A, Ke Y, El Idrissi A, Shen C H. Downregulation of GABA(A) beta subunits is transcriptionally controlled by Fmr1p. J Mol Neurosci 2012; 46:272-5.
10. D'Hulst C, Heulens I, Brouwer J R, et al. Expression of the GABAergic system in animal models for fragile X syndrome and fragile X associated tremor/ataxia syndrome (FXTAS). Brain research 2008.
11. El Idrissi A, Ding X H, Scalia J, Trenkner E, Brown W T, Dobkin C. Decreased GABA(A) receptor expression in the seizure-prone fragile X mouse. Neuroscience letters 2005; 377:141-6.
12. El Idrissi A, Yan X, L'Amoreaux W, Brown W T, Dobkin C. Neuroendocrine alterations in the fragile X mouse. Results Probl Cell Differ 2012; 54:201-21.
13. Hagerman R J, Sobesky W E. Psychopathology in fragile X syndrome. The American journal of orthopsychiatry 1989; 59:142-52.
14. Sobesky W E, Pennington B F, Porter D, Hull C E, Hagerman R J. Emotional and neurocognitive deficits in fragile X. Am J Med Genet 1994; 51:378-85.
15. Hagerman R J, Hills J, Scharfenaker S, Lewis H. Fragile X syndrome and selective mutism. Am J Med Genet 1999; 83:313-7.
16. Berry-Kravis E, Potanos K. Psychopharmacology in fragile X syndrome—present and future. Ment Retard Dev Disabil Res Rev 2004; 10:42-8.
17. Angkustsiri K, Wirojanan J, Deprey L J, Gane L W, Hagerman R J. Fragile X syndrome with anxiety disorder and exceptional verbal intelligence. Am J Med Genet A 2008; 146:376-9.
18. Shanahan M, Roberts J, Hatton D, Remick J, Goldsmith H. Early temperament and negative reactivity in boys with fragile X syndrome. J Intellect Disabil Res 2008; 52:842-54.
19. Bailey D B, Jr., Raspa M, Bishop E, Olmsted M, Mallya U G, Berry-Kravis E. Medication utilization for targeted symptoms in children and adults with fragile X syndrome: U S survey. Journal of developmental and behavioral pediatrics: JDBP 2012; 33:62-9.
20. Tranfaglia M R. Fragile X syndrome: a psychiatric perspective. Results Probl Cell Differ 2012; 54:281-95.
21. Erickson C A, Stigler K A, Posey D, McDougle C. Managing maladaptive behaviors in fragile X patients. Curr Psychiatry 2006; 5:80-92.
22. Rudolph U, Knoflach F. Beyond classical benzodiazepines: novel therapeutic potential of GABAA receptor subtypes. Nature reviews Drug discovery 2011; 10:685-97.
23. Alhambra C, Becker C, Blake T, et al. Development and SAR of functionally selective allosteric modulators of GABAA receptors. Bioorganic & medicinal chemistry 2011; 19:2927-38.
24. Kuribara H, Asahi T. Assessment of the anxiolytic and amnesic effects of three benzodiazepines, diazepam, alprazolam and triazolam, by conflict and non-matching to sample tests in mice. Nihon shinkei seishin yakurigaku zasshi=Japanese journal of psychopharmacology 1997; 17:1-6.
25. Zhou D, Sunzel M, Ribadeneira M D, et al. A clinical study to assess CYP1A2 and CYP3A4 induction by AZD7325, a selective GABA(A) receptor modulator—an in vitro and in vivo comparison. Br J Clin Pharmacol 2012; 74:98-108.
26. Henderson C, Wijetunge L, Kinoshita M N, et al. Reversal of disease-related pathologies in the fragile X mouse model by selective activation of GABA(B) receptors with arbaclofen. Science translational medicine 2012; 4:152ra28.
27. Kooy R F, D'Hooge R, Reyniers E, et al. Transgenic mouse model for the fragile X syndrome. Am J Med Genet 1996; 64:241-5.
28. Chen L, Toth M. Fragile X mice develop sensory hyperreactivity to auditory stimuli. Neuroscience 2001; 103:1043-50.
29. Romero-Zerbo Y, Decara J, el Bekay R, et al. Protective effects of melatonin against oxidative stress in Fmr1 knockout mice: a therapeutic research model for the fragile X syndrome. Journal of pineal research 2009; 46:224-34.
30. Mientjes E J, Nieuwenhuizen I, Kirkpatrick L, et al. The generation of a conditional Fmr1 knock out mouse model to study Fmrp function in vivo. Neurobiology of disease 2006; 21:549-55.
31. Liu Z H, Smith C B. Dissociation of social and nonsocial anxiety in a mouse model of fragile X syndrome. Neuroscience letters 2009; 454:62-6.
32. Moon J, Beaudin A E, Verosky S, et al. Attentional dysfunction, impulsivity, and resistance to change in a mouse model of fragile X syndrome. Behavioral neuroscience 2006; 120:1367-79.
33. Schaefer T L, Vorhees C V, Williams M T. Mouse plasmacytoma-expressed transcript 1 knock out induced 5-HT disruption results in a lack of cognitive deficits and an anxiety phenotype complicated by hypoactivity and defensiveness. Neuroscience 2009; 164:1431-43.
34. Schaefer T L, Lingrel J B, Moseley A E, Vorhees C V, Williams M T. Targeted mutations in the Na,K-ATPase alpha 2 isoform confer ouabain resistance and result in abnormal behavior in mice. Synapse 2011; 65:520-31.
35. Thomas A, Burant A, Bui N, Graham D, Yuva-Paylor L A, Paylor R. Marble burying reflects a repetitive and preservative behavior more than novelty-induced anxiety. Psychopharmacology (Berl) 2009; 204:361-73.

36. Veeraragavan S, Graham D, Bui N, Yuva-Paylor L A, Wess J, Paylor R. Genetic reduction of muscarinic M4 receptor modulates analgesic response and acoustic startle response in a mouse model of fragile X syndrome (FXS). Behavioural brain research 2012; 228:1-8.
37. Thomas A M, Bui N, Perkins J R, Yuva-Paylor L A, Paylor R. Group I metabotropic glutamate receptor antagonists alter select behaviors in a mouse model for fragile X syndrome. Psychopharmacology (Berl) 2012; 219:47-58.
38. Egashira N, Abe M, Shirakawa A, et al. Effects of mood stabilizers on marble-burying behavior in mice: Involvement of GABAergic system. Psychopharmacology (Berl) 2012.
39. Goebel-Goody S M, Wilson-Wallis E D, Royston S, Tagliatela S M, Naegele J R, Lombroso P J. Genetic manipulation of STEP reverses behavioral abnormalities in a fragile X syndrome mouse model. Genes, brain, and behavior 2012; 11:586-600.
40. Bourin M, Hascoet M. The mouse light/dark box test. European journal of pharmacology 2003; 463:55-65.
41. Crawley J, Goodwin F K. Preliminary report of a simple animal behavior model for the anxiolytic effects of benzodiazepines. PharmacolBiochemBehav 1980; 13:167-70.
42. Frankland P W, Wang Y, Rosner B, et al. Sensorimotor gating abnormalities in young males with fragile X syndrome and Fmr1-knockout mice. Molecular psychiatry 2004; 9:417-25.
43. Dahlhaus R, El-Husseini A. Altered neuroligin expression is involved in social deficits in a mouse model of the fragile X syndrome. Behavioural brain research 2010; 208:96-105.
44. Bhattacharya A, Kaphzan H, Alvarez-Dieppa A C, Murphy J P, Pierre P, Klann E. Genetic removal of p70 S6 kinase 1 corrects molecular, synaptic, and behavioral phenotypes in fragile X syndrome mice. Neuron 2012; 76:325-37.
45. Dunlop B W, Papp L, Garlow S J, Weiss P S, Knight B T, Ninan P T. Tiagabine for social anxiety disorder. Human psychopharmacology 2007; 22:241-4.
46. Skelton M R, Schaefer T L, Graham D L, et al. Creatine transporter (CrT; Slc6a8) knockout mice as a model of human CrT deficiency. PLoS One 2011; 6:e16187.
47. Brunskill E W, Ehrman L A, Williams M T, et al. Abnormal neurodevelopment, neurosignaling and behaviour in Npas3-deficient mice. Eur J Neurosci 2005; 22:1265-76.
48. Lindzey G, Winston H, Manosevitz M. Social dominance in inbred mouse strains. Nature 1961; 191:474-6.
49. Spencer C M, Alekseyenko O, Serysheva E, Yuva-Paylor L A, Paylor R. Altered anxiety-related and social behaviors in the Fmr1 knockout mouse model of fragile X syndrome. Genes Brain Behav 2005; 4:420-30.
50. D'Hooge R, Nagels G, Franck F, et al. Mildly impaired water maze performance in male Fmr1 knockout mice. Neuroscience 1997; 76:367-76.
51. Williams M T, Brown R W, Vorhees C V. Neonatal methamphetamine administration induces region-specific long-term neuronal morphological changes in the rat hippocampus, nucleus accumbens and parietal cortex. The European journal of neuroscience 2004; 19:3165-70.
52. Gibb R, Kolb B. A method for vibratome sectioning of Golgi-Cox stained whole rat brain. Journal of neuroscience methods 1998; 79:1-4.
53. Sholl D A. The Organization of the Cerebral Cortex. London: Methuen & Co.; 1956.
54. Shimono K, Baudry M, Ho L, Taketani M, Lynch G. Long-term recording of LTP in cultured hippocampal slices. Neural plasticity 2002; 9:249-54.
55. Curran C P, Nebert D W, Genter M B, et al. In utero and lactational exposure to PCBs in mice: adult offspring show altered learning and memory depending on Cyp1a2 and Ahr genotypes. Environ Health Perspect 2011; 119: 1286-93.
56. Hochberg Y, Benjamini Y. More powerful procedures for multiple significance testing. Statistics in medicine 1990; 9:811-8.

What is claimed is:

1. A method of alleviating a combination of Fragile X-associated symptoms comprising anxiety, impaired functional communication, inattention, sensory reactivity, aberrant eye gaze, aberrant impaired cognitive function, and compromised daily living skills, comprising administering to a subject in need thereof, a therapeutically effective amount of

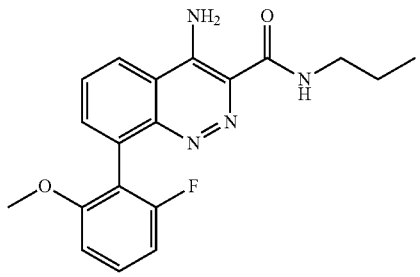 [SMILES: CCCNC(=O)c1nnc2c(-c3c(F)cccc3OC)cccc2c1N]

(4-amino-8-(2-fluoro-6-methoxy-phenyl)-N-propyl-cinnoline-3-carboxamide) or a pharmaceutically acceptable salt thereof.

2. The method of claim 1, wherein said method includes the co-administration of an agent selected from an atypical antipsychotics, lithium, a selective serotonin reuptake inhibitor (SSRI), a serotonin noradrenergic reuptake inhibitor (SNRI), non-S SRI non-SNRI serotonergic drug, a benzodiazepine, a glutamatergic drug, a GABA(B) modulator, opiate receptor modulators, endocannabinoid system modulators, anti-epileptics, alpha 2-agonists, mGlur5 antagonists, glutamatergic agents, GABA modulators, or a combination thereof.

3. The method of claim 1, wherein said method includes the co-administration of an agent selected from oxytocin, lithium, minocycline, or a combination thereof.

4. The method of claim 1, wherein said method includes the co-administration of a structured non-drug therapies including occupational therapy, speech therapy, language learning interventions, social skills training, cognitive behavioral therapy, discrete trial training, biofeedback, computerized cognitive training, or a combination thereof.

5. The method of claim 1, wherein said (4-amino-8-(2-fluoro-6-methoxy-phenyl)-N-propyl-cinnoline-3-carboxamide) or a pharmaceutically acceptable salt thereof is administered in a dose of from about 2 g bid to about 15 g bid.

6. The method of claim 1, wherein said (4-amino-8-(2-fluoro-6-methoxy-phenyl)-N-propyl-cinnoline-3-carboxamide) or a pharmaceutically acceptable salt thereof is administered orally.

7. The method of claim 1, wherein said (4-amino-8-(2-fluoro-6-methoxy-phenyl)-N-propyl-cinnoline-3-carboxamide) or a pharmaceutically acceptable salt thereof is administered nasally.

8. The method of claim 1, wherein said administration step is carried out until ERK phosphorylation is normalized.

9. The method of claim 7, wherein said ERK phosphorylation normalization is determined via measurement in the blood of a subject receiving said (4-amino-8-(2-fluoro-6-methoxy-phenyl)-N-propyl-cinnoline-3-carboxamide) or a pharmaceutically acceptable salt thereof.

* * * * *